(12) United States Patent
Lin et al.

(10) Patent No.: US 9,983,197 B2
(45) Date of Patent: May 29, 2018

(54) LOW-COST PORTABLE MICROFLUIDIC SYSTEM FOR CELL MIGRATION

(71) Applicant: University of Manitoba, Winnipeg (CA)

(72) Inventors: Francis Lin, Winnipeg (CA); Jiandong Wu, Winnipeg (CA)

( * ) Notice: Subject to any disclaimer, the term of this patent is extended or adjusted under 35 U.S.C. 154(b) by 443 days.

(21) Appl. No.: 14/425,139

(22) PCT Filed: Sep. 10, 2013

(86) PCT No.: PCT/CA2013/050697
§ 371 (c)(1),
(2) Date: Mar. 2, 2015

(87) PCT Pub. No.: WO2014/040185
PCT Pub. Date: Mar. 20, 2014

(65) Prior Publication Data
US 2015/0212070 A1    Jul. 30, 2015

Related U.S. Application Data

(60) Provisional application No. 61/701,231, filed on Sep. 14, 2012.

(51) Int. Cl.
*G01N 33/50* (2006.01)
*B01L 3/00* (2006.01)
(Continued)

(52) U.S. Cl.
CPC .... *G01N 33/5029* (2013.01); *B01L 3/502715* (2013.01); *G06K 9/00134* (2013.01);
(Continued)

(58) Field of Classification Search
CPC ......... B01L 2300/023; B01L 2300/027; B01L 2300/0663; B01L 2300/0864;
(Continued)

(56) References Cited

U.S. PATENT DOCUMENTS

2007/0090026 A1* 4/2007 Han ............... B01D 61/027
                                                           209/2
2010/0035292 A1* 2/2010 Levhenko ......... B01L 3/502746
                                                           435/29
(Continued)

OTHER PUBLICATIONS

Lin, F., "A Microfluidics-Based Method for Analyzing Leukocyte Migration to Chemoattractant Gradients." Methods in Enzymology, 2009, vol. 461, Chapter 15, pp. 333-347 ISSN 0076-6879.
(Continued)

*Primary Examiner* — Nathan A Bowers
*Assistant Examiner* — Lydia Edwards
(74) *Attorney, Agent, or Firm* — Ryan W. Dupuis; Ade and Company Inc; Kyle R. Satterthwaiter

(57) ABSTRACT

Low-cost and portable microfluidic systems are needed for cell migration research and Point of Care (POC) testing. This study introduces a low-cost and portable USB Microscope Microfluidic Chemotaxis Analysis System (UMCAS) for rapid analysis of cell chemotaxis studies. A standalone microfluidic gradient generator is also developed for rapid generation of chemical gradient in microfluidic device without need of any peripheral perfusion apparatus. A smart phone based application program was developed for the real-time remote monitoring of the migration data. This system is validated by observing the neutrophil migration in three different conditions: 1) medium control, 2) uniform IL-8 control, and 3) IL-8 gradient. The results show that neutrophils exhibit random migration in both medium and uniform IL-8 control experiments, while they show strong directional migration to the IL-8 gradient. These results successfully validated the developed UMCAS system.

7 Claims, 12 Drawing Sheets

(51) Int. Cl.
  *G06K 9/00* (2006.01)
  *G06T 7/00* (2017.01)
(52) U.S. Cl.
  CPC ........ *G06K 9/00147* (2013.01); *G06T 7/0012* (2013.01); *B01L 2300/023* (2013.01); *B01L 2300/027* (2013.01); *B01L 2300/0663* (2013.01); *B01L 2300/0864* (2013.01); *B01L 2400/0472* (2013.01); *G06T 2207/10056* (2013.01); *G06T 2207/20021* (2013.01); *G06T 2207/20036* (2013.01); *G06T 2207/30004* (2013.01)
(58) Field of Classification Search
  CPC ....... B01L 2400/0472; B01L 3/502715; G01N 33/5029; G06K 9/00134; G06K 9/00147; G06T 2207/10056; G06T 2207/20021; G06T 2207/20036
  USPC ........................................ 422/504; 435/287.1
  See application file for complete search history.

(56) References Cited

U.S. PATENT DOCUMENTS

| | | | | |
|---|---|---|---|---|
| 2011/0126279 | A1* | 5/2011 | Senshu | G11B 20/00086 726/16 |
| 2011/0253224 | A1* | 10/2011 | Linder | B01L 3/5027 137/2 |

OTHER PUBLICATIONS

Chin, C., D., et al. "Commercialization of microfluidic point-of-care diagnostic devices." Lab on a Chip, Jan. 27, 2012, vol. 12 pp. 2118-2134, ISSN 1473-0197.
Keller, R., Cell Migration During Gastrulation. Current Opinion in Cell Biology, 2005. 17(5): p. 533 41.
Matsubayashi, Y., et al., ERK Activation Propagates in Epithelial Cell Sheets and Regulates Their Migration During Wound Healing. Current Biology, 2004. 14(8): p. 731-5.
McDougall, S., et al., Fibroblast Migration and Collagen Deposition During Dermal Wound Healing: Mathematical Modelling and Clinical Implications. Philosophical Transactions A Math Phys Eng Sci, 2006. 364(1843): p. 1385-405.
Luster, A.D., R., Alon and U.H. Von Andrian, Immune Cell Migration in Inflammation: Present and Future Therapeutic Targets. Nature Immunology, 2005. 6(12): p. 1182-90.
Friedl, P. and Wolf K., Tumour-Cell Invasion and Migration: Diversity and Escape Mechanisms. Nat Rev Cancer, 2003. 3(5): p. 362-74.
Yamaguchi, H., Wyckoff, J. and Condeelis, J., Cell Migration in Tumors. Current Opinion in Cell Biology, 2005. 17(5): p. 559-64.
Boyden, S., The Chemotactic Effect of Mixtures of Antibody and Antigen on Polymorphonuclear Leucocytes. J. Exp. Med, 1962. 115: 453-66.
Zigmond, S., Ability of Polymorphonuclear Leukocytes to Orient in Gradients of Chemotactic Factors. The Journal of Cell Biology, 1977. 75(2 Pt 1): p. 606-16.
Lohof, A., et al., Asymmetric Modulation of Cytosolic cAMP activity Induces Growth Cone Turning. The Journal of Neuroscience, 1992. 12(4): p. 1253-1261.
Zicha, D., G. Dunn, and G. Jones, Analyzing Chemotaxis Using the Dunn Direct-Viewing Chamber. Methods in Molecular Biology, vol. 75, 1997. p. 449-457.
Nelson R. D., P.G. Quie, and R.L. Simmons, Chemotaxis Under Agarose: A New and Simple Method for Measuring Chemotaxis and Spontaneous Migration of Human Polymorphonuclear Leukocytes and Monocytes. The Journal of Immunology, 1975. 115(6): p. 1650-1656.
Lin, F. and Buther, T Cell Chemotaxis in a Simple Microfluidic Device. Lab on a Chip, 2006. 6(11): p. 1462-9.
Saadi, W., et al., A Parallel-Gradient Microfluidic Chamber for Quantitative Analysis of Breast Cancer Cell Chemotaxis. Biomed Microdevices, 2006. 8(2)p. 109-18.
Saadi, W., et al., Generation of Stable Concentration Gradients in 2D and 3D Environments Using a Microfluidic Ladder Chamber. Biomedical Microdevices, 2007. 9(5): p. 627-635.
Ahmed, T., T.S. Shimizu, and R. Stocker, Bacterial Chemotaxis in Linear and Nonlinear Steady Microfluidic Gradients. Nano Letters, 2010. 10(9): p. 3379-3385.
Lin, F. Chapter 15. A Microfluidics-Based Methodf or Chemoattractant Gradients. Methods in Enzymology, 2009. 461: p. 337-47.
Kim S., H.J., Kim and N.L. Jeon, Biological Applications of Microfluidic Gradient Devices. Integrative Biology, 2010. 2(11-12): p. 584-603.
Abhyankar, V.V., et al., Characterization of a Membrane-Based Gradient Generator for use in Cell-Signalling Studies. Lab on a Chip, 2006. 6(2): p. 389-393.
Si, G., et al., A Parallel Diffusion-Based Microfluidic Device for Bacterial Chemotaxis Analysis. Lab on a Chip. 2012. 12(7): p. 1389-1394.
Dertingre, S.K.W., et al., Generation of Gradients Having Complex Shapes Using Microfluidic Networks. Analytical Chemistry, 2001. 73(6): p. 1240-1246.

* cited by examiner

Original

Gaussian filter

Thresholding

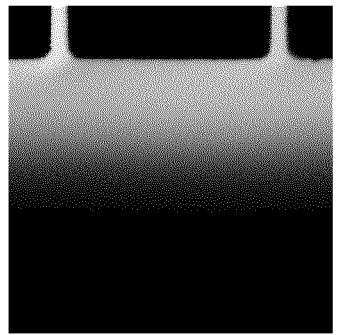
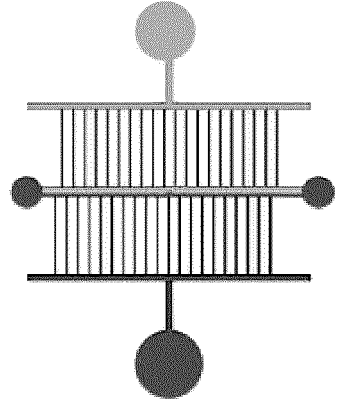
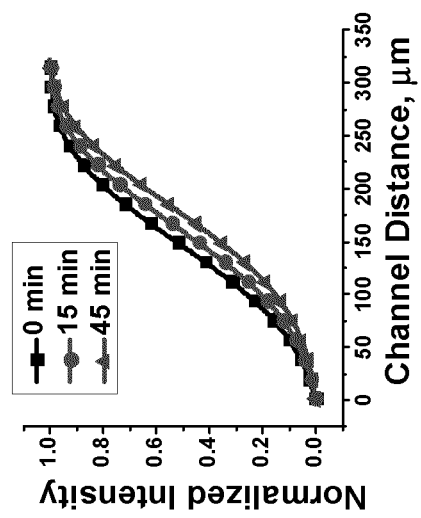

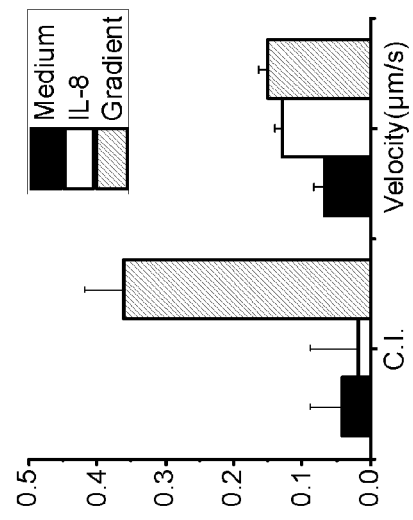
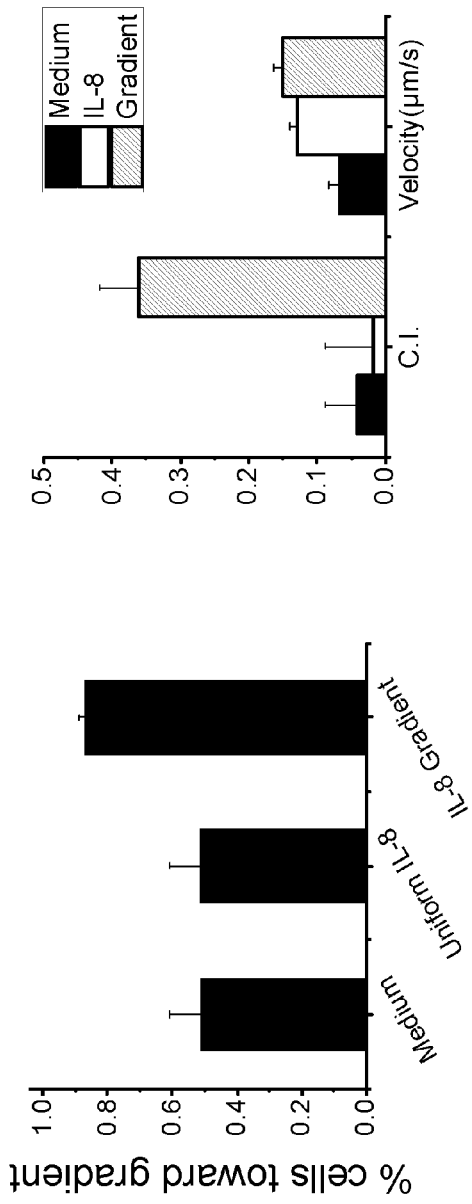
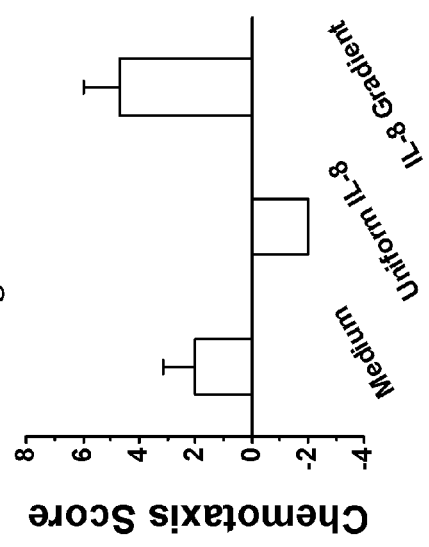

LOW-COST PORTABLE MICROFLUIDIC SYSTEM FOR CELL MIGRATION

FIELD OF THE INVENTION

The present invention relates to a microfluidic system including a portable housing supporting a microfluidic gradient device and an image capturing device therein to capture and transmit images of the microfluidic gradient device to the auxiliary computing device for cell migration studies, and more particularly the present invention relates to a configuration of microfluidic channels in the microfluidic device for generating a chemical gradient between source and sink wells by diffusion.

BACKGROUND

Many cells have the ability to sense the direction of external chemical signals and respond by polarizing and migrating towards chemoattractants. This phenomenon, called chemotaxis, has been shown to play an important role in embryogenesis [1], wound healing [2, 3], immune response [4] and cancer metastasis [5, 6]. In addition, cell migration and trafficking are closely associated with relevant physiological problems and diseases such as autoimmune diseases and cancers, and therefore has high clinical relevance. The ability to observe a single cell's response to a chemotactic environment is necessary in order to develop quantitative models to describe and predict chemotactic behaviors.

Conventionally, cell chemotaxis is measured in vitro by Boyden chamber or transwell assays and other free-diffusion based cell migration assays, such as under-agarose assay, micropipette-based assay, Dunn chamber, and Zigmond chamber [7-11]. Although widely used, these assays suffer from poorly controlled chemoattractant gradients and lack of capability for quantitative analysis. By contrast, development of microfluidic devices have been increasingly applied to cell migration studies owing to its ability to configure well-defined and stable chemical concentration gradients and the advantages in miniaturization, low reagent consumption and the potential for high-throughput experimentation[12-17]. Therefore, microfluidic devices offer a new experimental platform for quantitative cell migration and chemotaxis studies.

Most microfluidics-based cell migration and chemotaxis studies require complicated control instruments and specialized research facilities beside the microfluidic device, which is expensive and bulky. For example, to capture the cell migration images, a microscope and a digital camera are necessary. For chemotaxis experiments, checking the chemical gradient is a fundamental step before starting the experiment. Additional high power lamp is usually necessary for checking the gradient. As the external facilities are usually very expensive, it prevents many interested scientists or students to directly engage microfluidic cell migration research. Additionally, these systems are very impractical to use in a conventional clinical setting, which hampers its development for clinical applications.

To generate a stable gradient for the chemotaxis experiment, lots of microfluidic gradient generators have been developed. Those strategies can be roughly divided into two major classes, one is the flow-based device where molecules are mainly transported by the laminar flows [12]; the other is the free-diffusion based device where the molecules are mainly transported by the molecular diffusion without flows [18, 19]. Both types of devices are able to generate well defined gradients. The advantage of the flow-based chemotaxis device is the short gradient establishing time, stability and flexible gradient configurations. However this kind of devices usually requires external mechanical pumps to infuse the chemicals in a constant flow rate. This will increase the cost of the system and make the system inconvenient to set up. The advantage of the diffusion-based microfluidic device is that the cells are not subject to fluid flow induced shear stresses and less relies on external control systems. The disadvantage is that the gradient establishment time is long and less flexible to manipulate gradient profiles. Further efforts are needed to find a low-cost and easy strategy for rapid and stable gradient generation.

There are two main applications for the use of microfluidics in healthcare: POC testing and central laboratory diagnostics. Compared to the central laboratory diagnostics systems, the POC systems have lots of advantages; firstly it can be used in many places outside the laboratory, such as the patient's home, moving vehicles; secondly the time to result can be short; the cost of the test can be more affordable for patients. Because microfluidic devices are disposable, rapid in performing the test and require reduced amount of reagents, it is expect to find broad POC applications. A microfluidic system is usually composed by a disposable microfluidic chip and peripheral equipment (pumps, reader, etc.). In the specific cell migration studies, the cost of microfluidic chips can meet the requirement of POC testing. But the commercial peripheral equipments used to automatically capture and analyze the data are still expensive. For example, EZ-TAXIScan (ECI Inc., Japan) is a commercialized optical assay device for the quantitative measurement of cellular chemotaxis. This system, has a compact body but is expensive and requires special microfluidic chip, not allowing other customized chip designs.

The following references, incorporated herein by reference, relate generally to the present invention and are referred to throughout the current specification by number.
1. Keller, R., *Cell migration during gastrulation*. Curr Opin Cell Biol, 2005. 17(5): p. 533-41.
2. Matsubayashi, Y., et al., *ERK activation propagates in epithelial cell sheets and regulates their migration during wound healing*. Curr Biol, 2004. 14(8): p. 731-5.
3. McDougall, S., et al., *Fibroblast migration and collagen deposition during dermal wound healing: mathematical modelling and clinical implications*. Philos Transact A Math Phys Eng Sci, 2006. 364(1843): p. 1385-405.
4. Luster, A. D., R. Alon, and U. H. von Andrian, *Immune cell migration in inflammation: present and future therapeutic targets*. Nat Immunol, 2005. 6(12): p. 1182-90.
5. Friedl, P. and K. Wolf, *Tumour-cell invasion and migration: diversity and escape mechanisms*. Nat Rev Cancer, 2003. 3(5): p. 362-74.
6. Yamaguchi, H., J. Wyckoff, and J. Condeelis, *Cell migration in tumors*. Curr Opin Cell Biol, 2005. 17(5): p. 559-64.
7. BOYDEN, S., *The chemotactic effect of mixtures of antibody and antigen on polymorphonuclear leucocytes*. J Exp Med, 1962. 115: p. 453-66.
8. Zigmond, S., *Ability of polymorphonuclear leukocytes to orient in gradients of chemotactic factors*. J Cell Biol, 1977. 75(2 Pt 1): p. 606-16.
9. Lohof, A., et al., *Asymmetric modulation of cytosolic cAMP activity induces growth cone turning*. J. Neurosci., 1992. 12(4): p. 1253-1261.
10. Zicha, D., G. Dunn, and G. Jones, *Analyzing Chemotaxis Using the Dunn Direct-Viewing Chamber.* 1997. p. 449-457.

11. Nelson, R. D., P. G. Quie, and R. L. Simmons, *Chemotaxis Under Agarose: A New and Simple Method for Measuring Chemotaxis and Spontaneous Migration of Human Polymorphonuclear Leukocytes and Monocytes.* J Immunol, 1975. 115(6): p. 1650-1656.
12. Lin, F. and E. Butcher, *T cell chemotaxis in a simple microfluidic device.* Lab Chip, 2006. 6(11): p. 1462-9.
13. Saadi, W., et al., *A parallel-gradient microfluidic chamber for quantitative analysis of breast cancer cell chemotaxis.* Biomed Microdevices, 2006. 8(2): p. 109-18.
14. Saadi, W., et al., *Generation of stable concentration gradients in 2D and 3D environments using a microfluidic ladder chamber.* Biomedical Microdevices, 2007. 9(5): p. 627-635.
15. Ahmed, T., T. S. Shimizu, and R. Stocker, *Bacterial Chemotaxis in Linear and Nonlinear Steady Microfluidic Gradients.* Nano Letters, 2010. 10(9): p. 3379-3385.
16. Lin, F., Chapter 15. *A microfluidics-based method for chemoattractant gradients.* Methods Enzymol, 2009. 461: p. 333-47.
17. Kim, S., H. J. Kim, and N. L. Jeon, *Biological applications of microfluidic gradient devices.* Integrative Biology, 2010. 2(11-12): p. 584-603.
18. Abhyankar, V. V., et al., *Characterization of a membrane-based gradient generator for use in cell-signaling studies.* Lab on a Chip, 2006. 6(3): p. 389-393.
19. Si, G., et al., *A parallel diffusion-based microfluidic device for bacterial chemotaxis analysis.* Lab on a Chip, 2012. 12(7): p. 1389-1394.
20. Dertinger, S. K. W., et al., *Generation of gradients having complex shapes using microfluidic networks.* Analytical Chemistry, 2001. 73(6): p. 1240-1246.

SUMMARY OF THE INVENTION

An object of the present invention is to develop a low-cost portable microfluidic system for cell migration studies. A system has been developed as described herein that integrates a standalone microfluidic chip, a USB microscope and other optical controls, and the temperature control component, which are controlled by an integrated software for experiment operation and rapid data analysis. Furthermore, a wireless module was developed to allow remote data monitoring in real-time using a smartphone. This system is referred to herein as UMCAS, which stands for USB Microscope-based Microfluidic Chemotaxis Analysis System. The validation of UMCAS for cell migration studies was demonstrated by measuring neutrophil chemotaxis in different conditions. The developed UMCAS system provides a full solution for performing microfluidic cell migration and chemotaxis experiments or POC testing in a portable and inexpensive manner for both lab scientists and clinicians.

According to one aspect of the present invention there is provided a microfluidic system for use with an auxiliary computing device in cell migration assays, the system comprising:

a portable housing;

a primary light source received in the housing;

a microfluidic device arranged to generate a chemical gradient and introduce sample cells to the chemical gradient;

a support assembly arranged to support the microfluidic device in proximity to the primary light source within the housing;

an image capturing device supported in the housing in proximity to the support assembly so as to be arranged to capture images of the microfluidic device when supported on the support assembly for illumination by the primary light source;

the image capturing device comprising a USB peripheral device including a USB connector arranged to transfer the images from the image capturing device to the auxiliary computing device; and an operating program arranged to be executed on the auxiliary computing device which includes an image analysis tool arranged to process the images captured by the image capturing device so as to identify the sample cells from a remaining background portion of the captured images.

According to a second aspect of the present invention there is provided a microfluidic system for use with an auxiliary computing device in cell migration assays, the system comprising:

a portable housing;

a primary light source received in the housing;

a microfluidic device arranged to generate a chemical gradient and introduce sample cells to the chemical gradient;

a support assembly arranged to support the microfluidic device in proximity to the primary light source within the housing;

an image capturing device supported in the housing in proximity to the support assembly so as to be arranged to capture images of the microfluidic device when supported on the support assembly for illumination by the primary light source and transfer the images from the image capturing device to the auxiliary computing device; and an operating program arranged to be executed on the auxiliary computing device which including an image analysis tool arranged to:
  i) process the images captured by the image capturing device so as to identify the sample cells from a remaining background portion of the captured images;
  ii) divide each processed image into a plurality of divisions;
  iii) count a number of identified sample cells in each divisions; and
  iv) display the counts to a user in realtime as each image is captured by the image capturing device.

According to a third aspect of the present invention there is provided a method of performing a cell migration assay comprising:

providing an auxiliary computing device including an operating program executable thereon for processing captured images;

providing a portable assembly comprising i) a housing, ii) a primary light source received in the housing, iii) a microfluidic device received in the housing, iv) an image capturing device supported in the housing in the form of a USB peripheral device including a USB connector arranged to transfer captured images from the image capturing device to the auxiliary computing device;

supporting the microfluidic device in proximity to the primary light source within the housing;

generating a chemical gradient in the microfluidic device and introducing sample cells to the chemical gradient, using the image capturing device to capture images of the microfluidic device illuminated by the primary light source;

executing the operating program on the auxiliary computing device to process the images captured by the image capturing device and identify sample cells from a remaining background portion of the captured images.

According to a fourth aspect of the present invention there is provided a method of performing a cell migration assay comprising:

providing an auxiliary computing device including an operating program executable thereon for processing a captured image;

providing a portable assembly comprising i) a housing, ii) a primary light source received in the housing, iii) a microfluidic device received in the housing, and iv) an image capturing device supported in the housing;

supporting the microfluidic device in proximity to the primary light source within the housing;

generating a chemical gradient in the microfluidic device and introducing sample cells to the chemical gradient, using the image capturing device to capture images of the microfluidic device illuminated by the primary light source;

transferring the captured images from the image capturing device to the auxiliary computing device;

executing the operating program on the auxiliary computing device so as to:
  i) process the images captured by the image capturing device to identify the sample cells from a remaining background portion of the captured images;
  ii) divide each processed image into a plurality of divisions;
  iii) count a number of identified sample cells in each divisions; and
  iv) display the counts to a user in realtime as each image is captured by the image capturing device.

When the primary light source comprises a USB peripheral device having a USB input and the method may further include connecting the USB input of the primary fight source to the auxiliary computing device to receive electrical power for illuminating the primary light source. The USB connector of the image capturing device may be similarly used to transfer electrical power from the auxiliary computing device to the image capturing device.

The portable assembly preferably further comprises a heater element operated under control of the operating program to maintain temperature in proximity to the microfluidic device within a prescribed range. The heater may comprise a transparent thermal heater supported between microfluidic device and the primary light source.

Preferably the operating program on the auxiliary computing device is used to define a region of interest of the captured images and further processing the image in response to a defined boundary selected by a user.

Processing the captured image may be accomplished using a high-pass Guassian filter step and/or using a threshold method step.

The processing of the captured image may further use a morphology operation which includes an erosion step followed by a dilation step using a structuring element which is greater than a size of the sample cells.

Processing the captured image may also include cell localization on the captured images for each one of a plurality of sample regions by: i) sizing a slide window of the sample region to traverse the whole image such that the window is slightly larger than a size of the sample cells; ii) when the slide window moves, summing a gray intensity of each pixel in the region; iii) identifying the region as a candidate cell if the sum is greater than a prescribed threshold; iv) constructing a macroblock centered on the candidate cell; v) using a microblock which is the same size as the window to slide the macroblock with constant step size while the microblock with a maximum intensity sum is the region that the cell locates; and vi) setting the pixel intensity in the sample region to zero.

The captured image may also be processed so as to: i) divide each processed image into a plurality of divisions, ii) count a number of identified sample cells in each divisions, and iii) display the counts to a user in realtime as each image is captured by the image capturing device.

Preferably the counts of the identified sample cells per division of each processed image are graphically summarized in realtime as each image is captured by the image capturing device.

The auxiliary computing device may be further arranged to i) communicate wirelessly with a portable electronic device, and ii) display the counts of the identified sample cells per division of each processed image in realtime on the portable electronic device as each image is captured by the image capturing device.

The chemical gradient may also be illuminated using a secondary light source supported in the portable housing which has a greater intensity than the first light source. When the image capturing device includes a lens directed along a primary axis towards the microfluidic device, preferably the secondary light source is supported in the portable housing so as to be directed generally radially inwardly towards the microfluidic device in relation to said primary axis and so as to be adjustable about the primary axis in relation to the microfluidic device.

According to another aspect of the present invention there is provided a microfluidic device for generating a chemical gradient, the device comprising: i) a transparent substrate; ii) a gradient channel formed in the substrate including a first boundary and a second boundary which are opposed and spaced apart from one another in a gradient direction; iii) a first inlet well formed in the substrate so as to define a source well; iv) a plurality of first microfluidic channels formed in the substrate in communication between the first inlet well and the gradient channel at spaced apart positions along the first boundary; v) a second inlet well formed in the substrate so as to define a sink well; vi) a plurality of second microfluidic channels formed in the substrate in communication between the second inlet well and the gradient channel at spaced apart positions along the second boundary; and vii) at least one outlet well formed in the substrate so as to be in fluid communication with gradient channel at an intermediate location between the first and second boundaries; whereby a chemical gradient is arranged to be generated across the gradient channel by diffusion in the gradient direction between the first and second boundaries of a chemical introduced into the first inlet well.

Preferably the gradient channel is elongate in a longitudinal direction and the first and second boundaries extend in said longitudinal direction.

The microfluidic channels are preferably elongate in a lateral direction oriented transversely to the longitudinal direction of the gradient channel and perpendicularly to the first and second boundaries the gradient channel.

Preferably each inlet well communicates with a respective inlet channel oriented parallel to the first and second boundaries of the gradient channel.

The microfluidic channels are preferably equidistant in length between the respective inlet channels and the gradient channel.

Preferably each first microfluidic channel communicates with the gradient channel at a respective location along the first boundary which is offset in a longitudinal direction of the first and second boundaries in relation to locations of corresponding second channels along the second boundary.

The first and second inlet wells are preferably symmetrical about a longitudinal direction of the gradient channel in relation to one another.

Preferably said at least one outlet well comprises two outlet wells in communication with the gradient channel at longitudinally opposed ends of the first and second boundaries.

One embodiment of the invention will now be described in conjunction with the accompanying drawings in which:

BRIEF DESCRIPTION OF THE DRAWINGS

FIG. 3A schematically illustrates a design of a standalone microfluidic gradient generator with a simulated gradient;

FIG. 3B represents an image of FITC-Dextran gradient using a traditional microscope;

FIG. 3C is a plot of a gradient profile over time;

FIG. 3D is photographic representation of the device according to

FIG. 3A in which the two inlet reservoirs are filled with food coloring dye solutions;

FIG. 5A represents a percentage of the cells migrated towards the gradient by manual cell tracking analysis according to neutrophil chemotaxis analysis using the system of the present invention;

FIG. 5B represents Chemotactic Index (C.I.) and speed by manual cell tracking analysis according to neutrophil chemotaxis analysis using the system of the present invention;

FIG. 5C represents automated cell counting and digital scoring analysis according to neutrophil chemotaxis analysis using the system of the present invention;

In the drawings like characters of reference indicate corresponding parts in the different figures.

DETAILED DESCRIPTION

Figure 7:
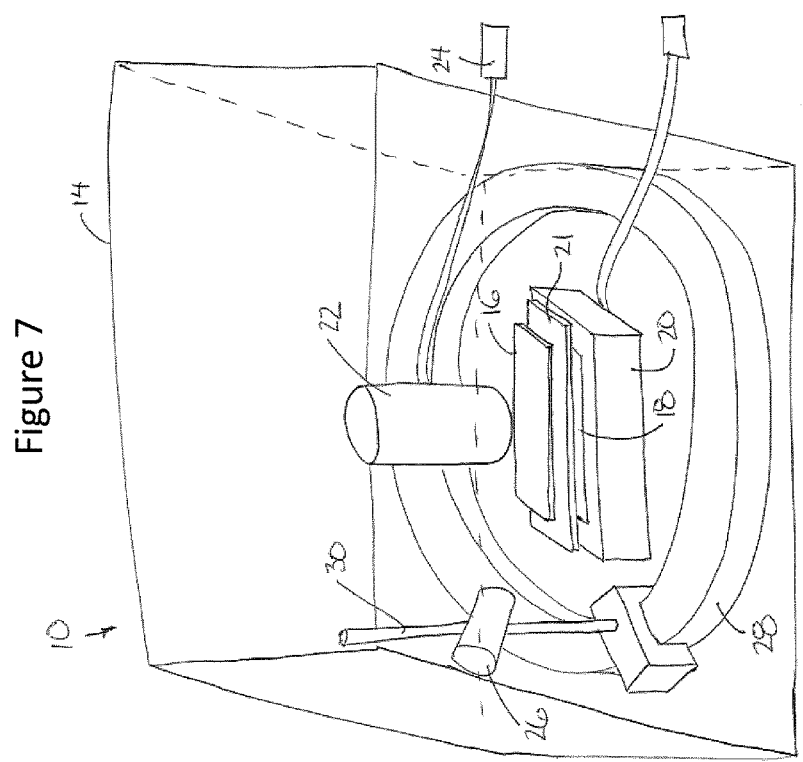
FIG. 7 is a schematic representation of the microfluidic system.

A microfluidic system 10 is described herein which is generally arranged for use with an auxiliary computing device (for example a laptop computer) in cell migration assays. As shown schematically in FIG. 7, the system includes a portable housing 14 forming a complete and full enclosure about a hollow interior which receives a microfluidic device 16 arranged to generate a chemical gradient and introduce sample cells to the chemical gradient therein.

A primary light source 18 is provided in the housing and a support assembly 20 supports the microfluidic device 16 in proximity to the primary light source 18. A transparent thermal heater 21 is supported between microfluidic device and the primary light source. The primary light source is a USB peripheral device having a USB input arranged for connection to the auxiliary computing device so as to receive electrical power for illuminating the primary light source.

An image capturing device 22 comprising a USB peripheral device includes a USB connector 24. The image capturing device supported in the housing in proximity to the support assembly so as to be arranged to capture images of the microfluidic device when supported on the support assembly for illumination by the primary light source. The USB connector 24 connects to the auxiliary computing device to transfer the images from the image capturing device to the auxiliary computing device and to transfer electrical power from the auxiliary computing device to the image capturing device.

An operating program is arranged to be executed on the auxiliary computing device which including an image analysis tool arranged to process the images captured by the image capturing device so as to identify the sample cells from a remaining background portion of the captured images.

As described in further detail below the image analysis tool is arranged to define a region of interest of the captured images prior to further image processes in response to a defined boundary selected by a user. Furthermore the image analysis tool is arranged to divide each processed image into a plurality of divisions, count a number of identified sample cells in each divisions, and display the counts to a user in realtime as each image is captured by the image capturing device. The image analysis tool is then arranged to graphically summarize the counts of the identified sample cells per division of each processed image in realtime as each image is captured by the image capturing device.

The image analysis tool is also arranged to communicate wirelessly with a portable electronic device, for example a smartphone, and display the counts of the identified sample cells per division of each processed image in realtime as each image is captured by the image capturing device. A further component of the system thus comprises an application which is executable on a mobile device such as a smartphone for receiving data from the auxiliary computing device and displaying the data to a user in realtime on a display of the smartphone.

The heater is also arranged to be operated under control of the operating program to maintain temperature in proximity to the microfluidic device within a prescribed range.

A secondary light source 26 is also supported within the portable housing. The secondary light source has a greater intensity than the first light source so as to be arranged for illuminating the chemical gradient. A primary axis is defined as the direction along with the lens of the image capturing device is directed towards the microfluidic device on the support assembly. The secondary light source is supported in the portable housing so as to be directed generally radially inwardly towards the microfluidic device in relation to the primary axis of the lens. A circular track 28 about the primary axis and an adjustable height stand 30 which rotates about the track 28 permit the secondary light source to be angularly adjustable about the primary axis and adjustable in height in relation to the microfluidic device.

Figure 8:
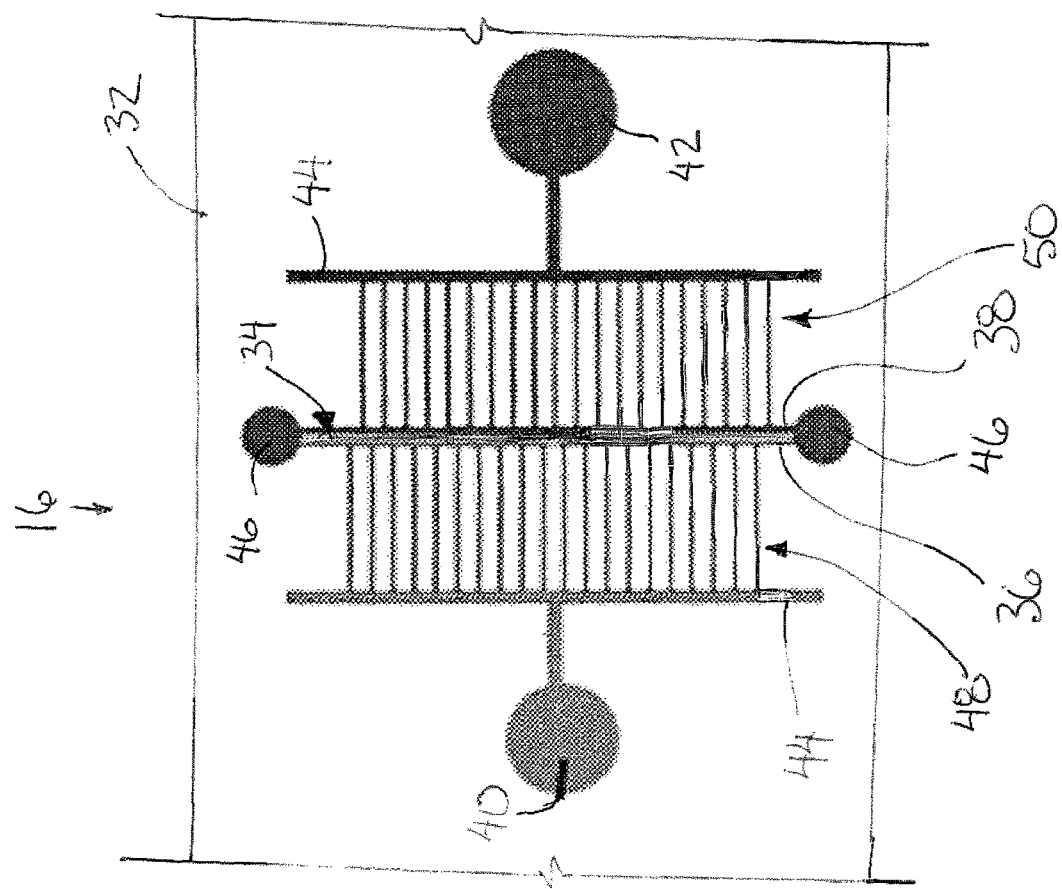
FIG. 8 is a schematic representation of the microfluidic device for generating the chemical gradient.

The microfluidic device is shown in greater detail in FIG. 8 and includes a transparent substrate 32 which is formed to define a plurality of passages therein in a generally common plane along one side of a first layer. A second layer bonded to the first layer encloses the channels and passages. The passages include a gradient channel 34 formed in the substrate which is elongate in a longitudinal direction to define a first boundary 36 and a second boundary 38 which are parallel and opposite from one another and extend in the longitudinal direction between opposing ends of the gradient channel. The first and second boundaries are spaced apart from one another in a gradient direction. As shown in FIG. 8, the gradient channel formed in the substrate is elongate in a longitudinal direction with the first boundary and the second boundary spanning a full length of the gradient channel in the longitudinal direction. More particularly, the first boundary and the second boundary are spaced apart from one another in a gradient direction so as to define a single chamber that is uniform between the first and second boundaries along a length of the gradient channel in the longitudinal direction.

A first inlet well 40 formed in the substrate defines a source well offset laterally outwardly from the first boundary of the gradient channel. Similarly, a second inlet well 42 is formed in the substrate to define a sink well offset laterally outwardly from the second boundary of the gradient channel. Both inlet wells are generally centered in the longitudinal direction of the gradient channel and communicates with a respective inlet channel 44 oriented parallel to and spaced laterally outwardly from respective ones of the first and second boundaries of the gradient channel. The first and second inlet wells 40 and 42, together with the respective inlet channels 44 are symmetrical about a central longitudinal axis of the gradient channel in relation to one another. The first inlet channel is thus elongate in the longitudinal direction of the gradient channel so as to lie parallel to and spaced outwardly from the first boundary of the gradient channel while defining a single chamber that is uniform across a width and along a length of the chamber in the longitudinal direction. Similarly, the second inlet channel is elongate in the longitudinal direction of the gradient channel so as to lie parallel to and spaced outwardly from the second boundary of the gradient channel while defining a single chamber that is uniform across a width and along a length of the chamber in the longitudinal direction.

Two outlet wells 46 are also formed in the substrate in fluid communication with the gradient channel at the longitudinally opposed ends of the gradient channel between the first and second boundaries of the gradient channel.

A plurality of first microfluidic channels 48 are formed in the substrate in communication between the first inlet channel of the first inlet well and the gradient channel at spaced apart positions along the first boundary. Similarly a plurality of second microfluidic channels 50 are formed in the substrate in communication between the second inlet channel of the second inlet well and the gradient channel at spaced apart positions along the second boundary.

The microfluidic channels 48 and 50 are elongate in a lateral direction oriented perpendicularly to the longitudinal direction of the first and second boundaries of the gradient channel. The microfluidic channels are equidistant in length between the respective inlet channels and the gradient channel due to the parallel relationship between the inlet channels and the gradient channel. The first and second microfluidic channels are offset in the longitudinal direction relative to one another such that each first microfluidic channel communicates with the gradient channel at a respective location along the first boundary which is offset in the longitudinal direction of the first and second boundaries in relation to locations of corresponding second channels along the second boundary.

When a chemical is introduced into the first inlet well, the configuration of the channels permits a chemical gradient to be generated across the gradient channel solely by diffusion in the gradient direction between the first and second boundaries.

Materials and Methods

1. System Assembly

The detailed design of UMCAS is shown in FIG. 1. The microfluidic system is composed by a USB webcam microscope (VMS-004D, 400× magnification, Veho, UK), an adjustable back-light microscope stand (DP-M06, Oriental inspariration limited company) and a high lumina blue LED (Blue Rebel LED, 470 nm, 58 lm @700 mA, LUXEON STAR LEDs). The microscope stand has a webcam holder, a up and down knob to adjust the distance between the microscope and object, a mini USB port to connect PC to supply power to LED backlight source, a LED backlight source and brightness control knob and a removable X&Y crossed to slightly adjust the position of the sample. The transparent cover in the head of microscope was removed so the lens is close enough to the object that would help to get better focus. To assemble the system, the microscope stand was fixed on the bottom board of the box. The USB microscope was clipped on the stand. A transparent thermal heater was taped on the glass stage of the stand to control the temperature for the microfluidic device. The high lumina blue LED was contacted with a condenser lens to focus the light beam. Then the LED module was contacted to an iron heat sink and the sink was fixed to an angle adjustment module. This module was composed of a metal ring in the bottom which can rotate around the microscope stand. A metal bar was inserted into the ring and another metal bar was hinged to this vertical bar. This kind of setup can realize multi dimension adjustment to find a best angle for the gradient checking. The adjustable back light in the microscope stand can help to get a clear cell image. The system was connected to computer by USB cables before starting the experiment.

2. Device Fabrication

The microfluidic device is fabricated using the standard soft-lithography method as described in previous paper [20].

Firstly, a transparency mask was printed using a high-resolution printer from a Freehand file (Adobe Systems Inc.). The master was then fabricated at The Nano Systems Fabrication Laboratory (NSFL) at the University of Manitoba. A silicon wafer is coated with a ~100 μm high photo resist (SU8-2075, MicroChem, MA). The design was patterned on the wafer through the transparency mask by UV processing. PDMS replicas were fabricated by molding PDMS (Dow Corning, MI) against the master. The surface of the PDMS replica and a clean glass slide were treated with air plasma for 1 min (PDC-001, Harrick Scientific, NY) and bonded together to make the microfluidic channels.

Figure 3E:
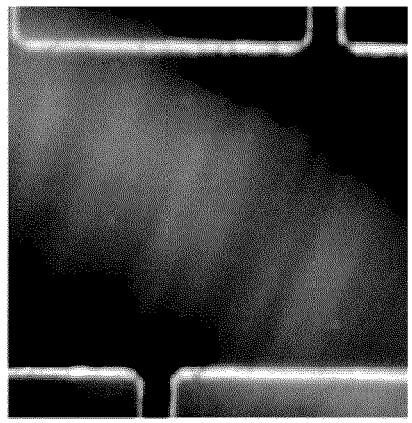
FIG. 3E is a captured image of the food-coloring dye gradient taken by system according to the present invention.

The design of the standalone gradient generator is shown in FIG. 3A. First the device is molded off its respective patterned wafer and cut out, punching out the appropriate wells. The source and sink wells are cut out with a puncher to create wells with a diameter of approximately 8 mm. The two outlet wells at the ends of the central channel are punched out to create 3 mm wide wells and the device is then bonded to a 50 mm×75 mm glass slide by air plasma.

3. Neutrophils Isolation and Device Preparing

Human whole blood was obtained from healthy volunteers. The mononuclear cells and plasma were removed from the whole blood using standard gradient centrifugation method. Then Dextran sedimentation was used to remove most of the RBC's in the remaining part of blood. The remaining RBC's were lysed by shocking the cells using 0.2% saline buffer for 30 seconds. Isolated neutrophils were washed with 0.85% saline buffer for two times and resuspended in culture medium (RPMI-1640 GLUTAMAX medium) before using.

Microfluidic devices are first coated with human fibronectin (BD Biosciences, MA) for one hour and then blocking is done using a 0.4% BSA in RPMI-1640 solution for another hour before the device is used for an experiment. Small amounts of concentrated neutrophil suspensions are added to the outlet wells to allow for attachment to the coated surfaces of the central channel. After sufficient cell loading, all wells (source, sink, and outlets) are completely emptied and new solution is added. 25 uL of media is added to each outlet well and the device is then placed on the thermal clear heater, maintained at 37° C. 150 uL of chemokine solution and 145 uL of RPMI-1640 media are added to the source and sink respectively and simultaneously using two pipettes. The gradient is visualized using the blue LED light and FITC-Dextran that is present in the solution in the source well. FITC-Dextran is used due to its similar molecular weight to the chemokine used (IL-8, a potent chemoattractant for neutrophils).

4. System Operation

UMCAS was connected to a computer by two USB cables. One is used for the image data transfer. The other one is used to supply power for the light source inside the stand. The UMCAS software is then opened and it will connect to the microscope automatically. The microfluidic device which was previously prepared was put on the stage under the USB microscope. Turn on the light source of the stand. Adjust the focus and make sure the cells can be watched clearly in the software. Turn off the light of the stand. Turn on the blue LED and check the gradient. Once the gradient is stable, the blue LED is turned off. The LED in the stand is turned on and cell migration could be observed. For remote monitoring, a smartphone application is opened and connected to the UMCAS software by BLUETOOTH protocol. Then the Region of Interest (ROI) in the channel is selected and the analysis starts. UMCAS software will automatically capture the time-lapse images and display the cell distribution of each frame. The result can also be shown in real-time in the smartphone.

5. Data Analysis 5.1 Manual Tracking Analysis

The data was analyzed by two methods, the traditional manual tracking method and the automatic analysis based on cell distribution. For the tradition manual method, time-lapse images of cell migration were captured by the UMCAS software. The cells were tracked using the "Manual Tracking" plug-in in NIH ImageJ. The tracking data were then exported to Excel and Origin for analysis. The movement of cells was quantitatively evaluated by (a) the Chemotaxis Index (C.I.), which is the ratio of the displacement of cells toward the chemical gradients to the total migration distance, presented as the average value±standard error of the mean (SEM). (b) the average velocity (V), calculated as $d/\Delta t$ and presented as the average value±SEM of all cells; and (c) percentage of cells migrate towards the gradient direction, also presented as average value±SEM.

5.2 Cell Distribution Analysis

The other method presented here doesn't need the labor-intensive manual tracking process. The whole process was done by the UMCAS software automatically. To do the cell distribution analysis, cells must be firstly segmented from the background. This was accomplished by two image processing steps.

5.2.1 Image Pre-Processing

Figure 2A:
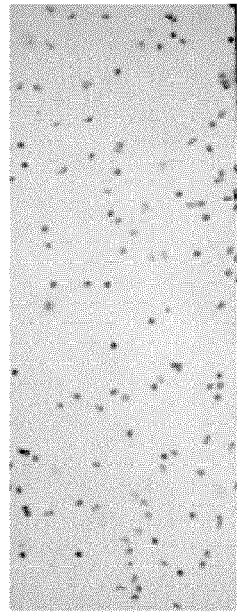
FIGS. 2A through 2F illustrate various steps of cell segmentation and distribution analysis.
Figure 2B:
Figure 2C:
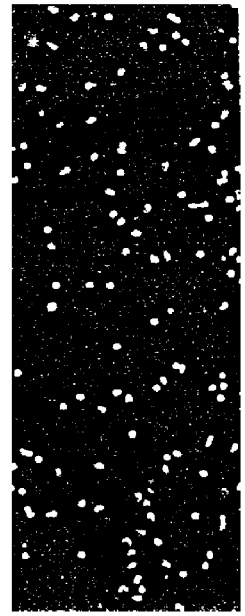
Figure 2D:
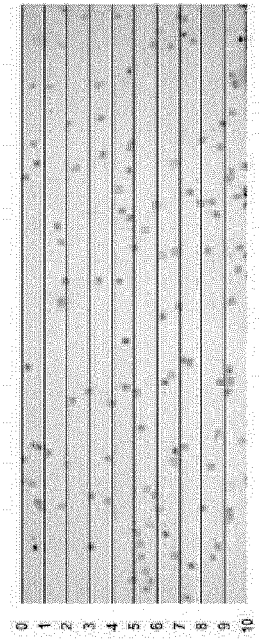

The image preprocessing is used to acquire soundary images. Normally, morphology operations and median filter provided by Matlab image processing toolbox are sufficient to smooth the images. However, due to the limitation of portable web cameras, considerable negative effects are introduced in the images. The original cell image captured by the USB microscope is presented in FIG. 2A. In this application, the image was firstly processed by high-pass Gaussian filter (FIG. 2B). Then a threshold method was applied to enhance the contrast of the image (FIG. 2C). After that the morphology operations was applied to remove small spot noises in the image. Morphology operation is composed of erosion followed by dilation using a structuring element which could be adjusted slightly larger than the size of the cell. The result after morphology operation was shown in FIG. 2D.

5.2.2 Cell Localization

Figure 2E:
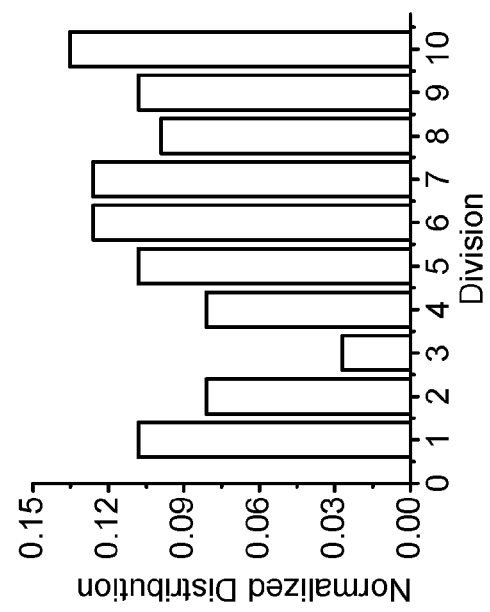

After preprocessing the images, a user can do the cell localization. There are four key steps: 1) design a slide window to traverse the whole image. The size of the window is slightly larger than the size of a cell; 2) when the window moves, sum the gray intensity of each pixel in this region. If the sum is greater than a threshold T, this region is probably a cell named candidate cell; 3) constructs a Macroblock centered on the candidate cell, and then uses a microblock which is the same size with the window to slide the Macroblock with constant step size. The microblock with maximum intensity sum is the region that the cell locates; 4) to avoid duplicate search, the pixels intensity in this region are set as 0. The final result after cell localization was presented in FIG. 2E.

Figure 2F:
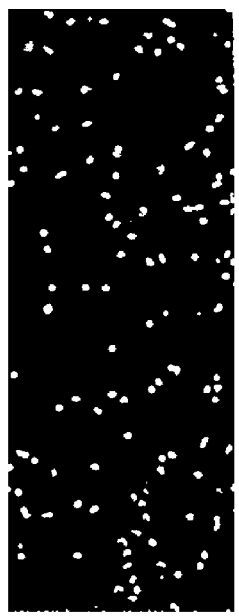

After cell localization, the whole channel is split into ten divisions towards the gradient direction. The cell number in each division is counted. The numbers are then normalized and shown in a bar diagram (FIG. 2F).

6. Remote Monitoring

The remote monitoring module is based on the wireless communication between the application program in a smart phone (Nexus S, Google Company) and the UMCAS software in the laptop. The smart phone has a version 2.3 android operating system. The UMCAS software launches a connection requirement and the smart phone app accepts the requirement. After the connection is created, the Matlab program starts to send the cell distribution data to the smart phone through Bluetooth SPP protocol. And once the smart phone received the data, it draws the data on the screen.

Results

1. Cost Comparison

Traditional microfluidic cell migration systems require stationary imaging facilities within a research lab. In comparison, UMCAS was assembled into a box with the side dimension of ~50 cm and the total weight of ~10 kg. Two carrying handles were installed on the side of the box. A hole was drilled in the back of the box to allow cable connections from UMCAS to the external laptop computer. A cable storage pocket was mounted next to the cable hole in the back of the box. The top and front windows of the box are transparent and removable. This design made UMCAS truly portable and easy to set up the experiment. The required imaging facility for traditional microfluidic cell migration systems typically includes a fluorescent microscope, a CCD camera, syringe pumps (if fluid perfusion is required for the microfluidic device) and a temperature control system. As estimated in Table 1, these instruments will easily cost a minimum of $14,000 for basic system configuration. In clear comparison, the total hardware cost for the current prototype version of UMCAS is less than $800 including material costs for the USB microscope, microscope stand, LED and heater/controller, plus the material and labour costs for making the box and assembling the system in the machine shop of the Department of Physics and Astronomy at the University of Manitoba. This low cost for hardware components of the system makes UMCAS affordable to cell migration researchers in need of a flexible and inexpensive solution for performing microfluidic cell migration experiments. In the current prototype version of UMCAS, a significant portion of the total cost (~60%) resulted from the initial costs of the custom-designed and fabricated box. This cost is expected to significantly reduce for duplicating the developed UMCAS with the established box design and fabrication/system assembly procedures, and by selecting more cost-efficient materials.

TABLE 1

Table 1 Cost comparison of the traditional system and UMCAS.

| System | Component | Cost |
| --- | --- | --- |
| Traditional system | Microscope | >$10000 |
| | Arc lamp | >$ 2000 |
| | CCD camera | >$ 500 |
| | Syringe pump | >$ 2000 |
| | Heater | >$ 160 |
| | Total | >$14000 |
| UMCAS | USB microscope | $ 99 |
| | LED lamp | <$ 50 |
| | Microscope stand | $ 35 |
| | Heater | $ 160 |
| | Box | $ 460 |
| | Total | <$ 800 |

2. Gradient Generation

Figure 3F:
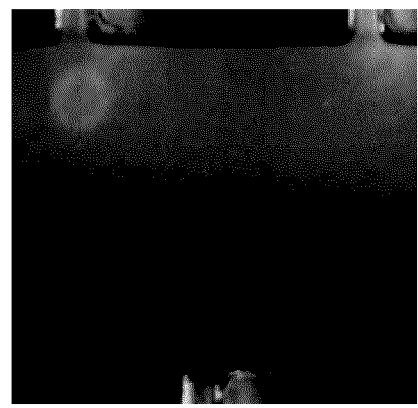
FIG. 3F is a captured image of the FITC-Dextran gradient using the system according to the present invention.
Figure 3D:
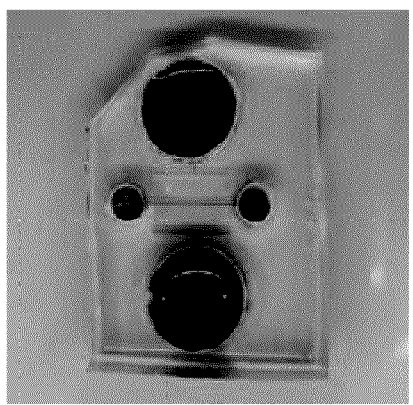
Figure 4A:
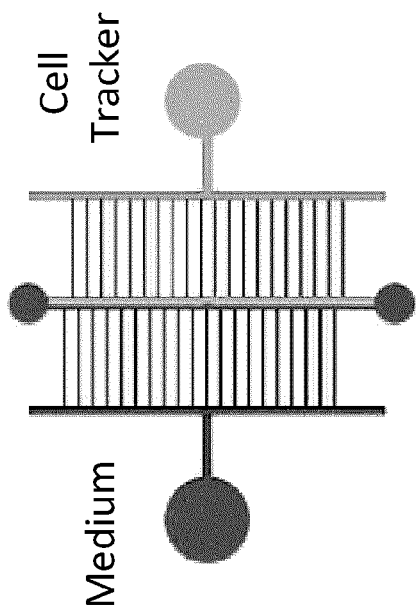
FIG. 4A illustrates live cell labeling by a cell tracker gradient in the standalone device in which a cell tracker solution and the medium were added to wells to create a cell tracker gradient in the gradient channel.
Figure 4B:
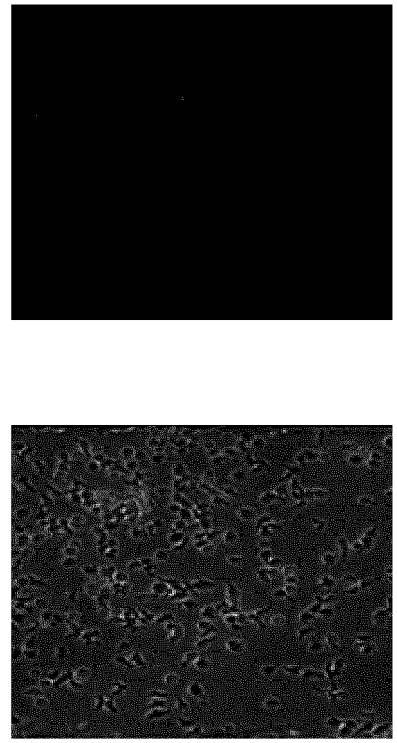
FIG. 4B shows the initial distribution of the cells according to FIG. 4A in the left image and shows increased labelling of cells toward the cell tracker gradient after 30 min exposure in the right image.
Figure 6A:
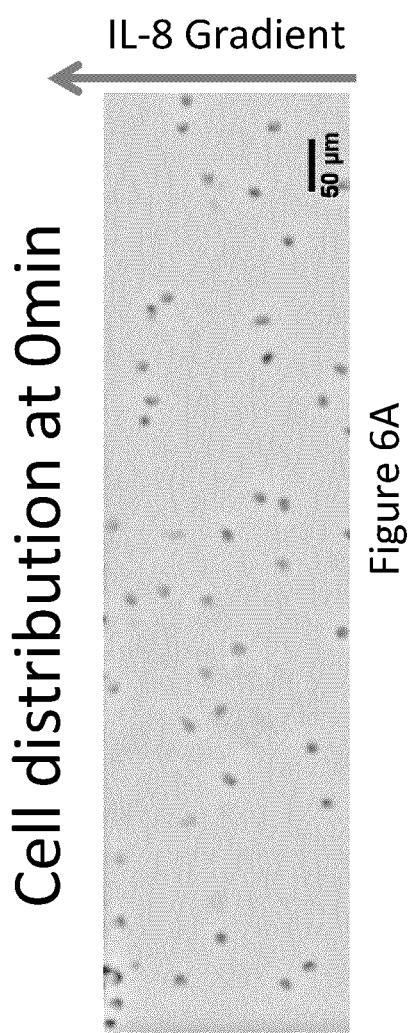
FIG. 6A represents a cell image captured by the system of the present invention at the 0th min when performing automated cell distribution and tracking analysis of neutrophil chemotaxis using an IL-8 gradient.
Figure 6B:
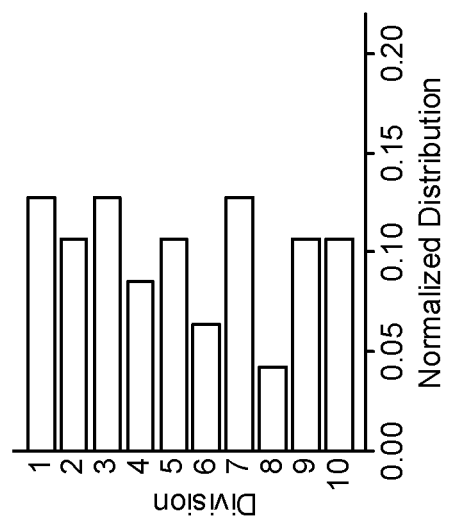
FIG. 6B represents a corresponding normalized cell distribution according to FIG. 6A.
Figure 6D:
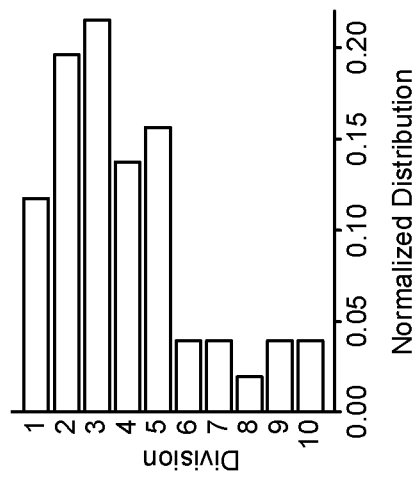
FIG. 6D represents a corresponding normalized cell distribution according to FIG. 6C.
Figure 6C:
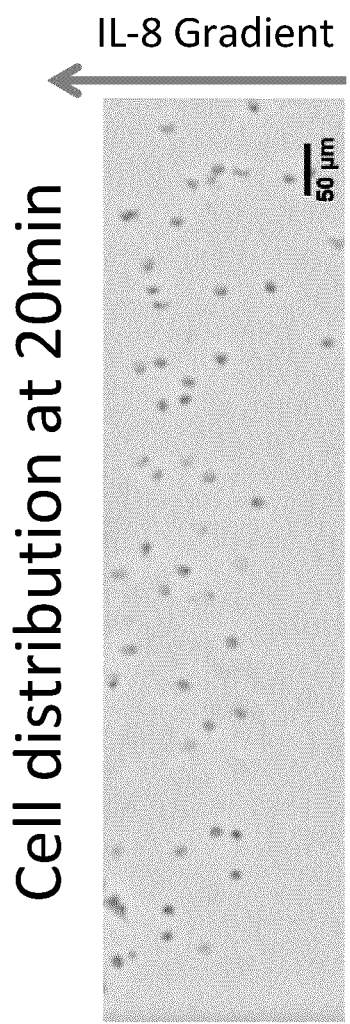
FIG. 6C represents a cell image captured by the system of the present invention at the 20th min when performing automated cell distribution and tracking analysis of neutrophil chemotaxis using an IL-8 gradient.

Gradient generation using the developed standalone microfluidic device was characterized by measuring FITC-Dextran 10 kDa intensity profile in the center gradient channel. Following the solution adding protocol as detailed in the Materials and Methods section, FITC-Dextran gradient was monitored by fluorescent time-lapse microscopy. The results show that a FITC-Dextran gradient was established in the center gradient channel in less than 5 min and maintained stable for at least 45 min (FIG. 3 B-C), which is at least sufficient for experiments with fast migratory cells such as neutrophils and T lymphocytes To validate that the developed standalone device can generate functional chemical gradient, a cell-tracker gradient was created in the device to label human T cells (FIG. 4). T cells were uniformly loaded to the center gradient channel. After 30 min exposure to the cell tracker gradient, T cells were increasingly labelled toward the cell tracker gradient as visualized by fluorescent microscopy. This result confirmed us that the developed microfluidic gradient device is suitable for live cell experiments.

3. Cell Observation

To validate the USB microscope for observing the cells, first cells were loaded into the microfluidic and the device was put on the stage of the microscope stand under the USB microscope. After adjusting the focus, cells could be observed as show in FIG. 2A. The quality of the cell image was not as good as using a traditional microscope and there was a bright part existing in the middle of the image, however, this was mostly caused by the unevenness of the back light source in the stand. Another possible reason is that the thermal clear heater which was fixed on the stand could also reduce the transparency by 30%. Although the image quality is not good enough, for manual tracking this would not be a problem because the cells can still be distinguished from the background clearly by eyes. For automatic analysis, this also would not be a problem because this issue was overcome by developing the filtering algorithm in the software to decrease the noise and increase the analysis accuracy. To demonstrate that this issue could also be fixed by using more intense and even light source and precisely align the camera, a small microscope was modified in a lab by replacing the objective of the microscope by the USB microscope. The device was put on the microscope stand without the heater and the cell quality was observed to be much better because the light source was much better in the microscope. To decrease the effect of the thermal clear heater, the heater could just be removed for some cells that are less sensitive to temperature such as Dicty cells. For the cells which demand the temperature control other types of heaters could be used that do not affect the image (heat box, on-chip heater, circulating water based, etc) but that will increase the cost.

4. Software Interface

Figure 1B:
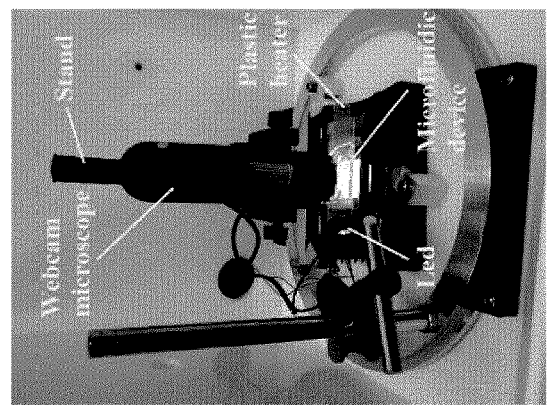
FIG. 1B illustrates components inside the housing of the system.
Figure 1A:
FIG. 1A is a photographic representation of the whole system according to the present invention referred to herein as UMCAS.
Figure 1D:
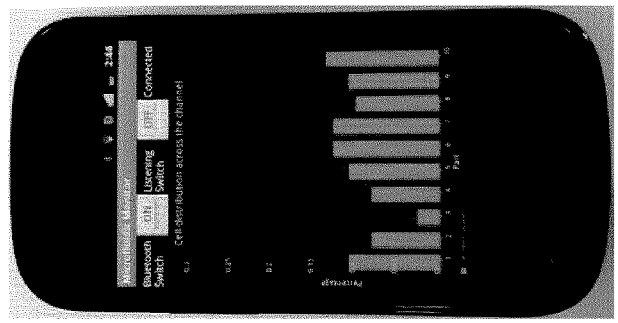
FIG. 1D illustrates an interface executable as an application on a smartphone for real-time remote data monitoring.
Figure 1C:
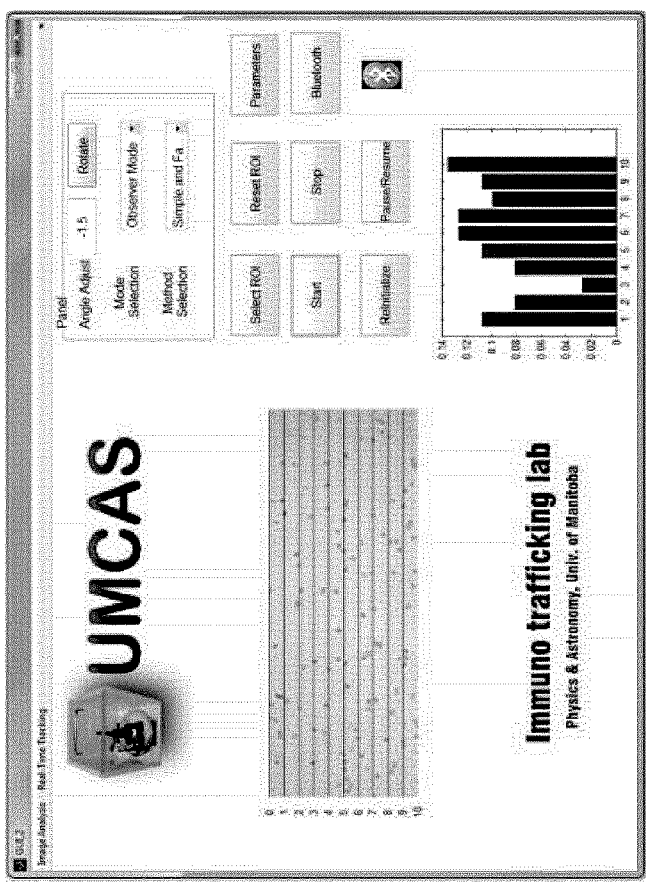
FIG. 1C illustrates an interface of the control and analysis software.

The interface the UMCAS software is shown in FIG. 1C. The interface allows user interaction through the auxiliary computing device with the operating program executable on the auxiliary computing device. The software has the basic functions such as image displaying, image rotation and ROI selection. FIG. 1D shows the application interface in the smart phone.

5. Validation of UMCAS for Neutrophil Migration Analysis

To ultimately validate the UMCAS for cell migration and chemotaxis studies, migration experiments were performed on human blood neutrophils over 20 min period using the UMCAS with a medium control, a uniform 12.5 nM IL-8 field, or a 12.5 nM IL-8 gradient. The cell migration images were analyzed by traditional single-cell tracking analysis. The results clearly show random cell migration in medium control and uniform IL-8, but strong chemotaxis toward the IL-8 gradient, as measured by the percentage of cells that moved toward the gradient and by the Chemotactic Index (FIG. 5A-B). As expected, cells migrated at higher speed in the uniform IL-8 or the IL-8 gradient compared with the medium control (FIG. 5B). These results validated effective neutrophil migration and chemotaxis experiments in the UMCAS. The manual tracking analysis allowed visual inspection of the experiment to check if there was i) a significant change in the total cell number in the time-lapse images; ii) if there was significant bias in the initial cell distribution; and iii) if there were too many non-migrating cells or flowing cells in the background. These data were used to determine the suitability of the experiment for the automated cell distribution and digital scoring analysis.

To validate the real-time chemotaxis analysis in UMCAS, automated cell distribution and digital scoring analysis in the UMCAS software were applied to the same neutrophil migration experiments. The results show that the image processing method can correctly identify and count cells in the microfluidic channel (FIG. 2). To enable a rapid chemotaxis analysis report without single-cell tracking, the cell distribution was analyzed in equally space divisions across the center gradient channel and along the gradient direction. Ideally, the shifted cell distribution toward the gradient will indicate chemotaxis (FIG. 6A-D). However, the cell distribution analysis itself was often affected by the initial cell loading and the background non-migrating or flowing cells. Therefore, a digital scoring method was developed to compare the change of cell distribution over the experiment period in each division with the focus on the sign of change, but not the absolute change level. Furthermore, the digitized scores were summed up for the left-side divisions and the right-side divisions and then the difference of the summed right-side score and the left-side score were compared to enhance the comparison.

Figure 6E:
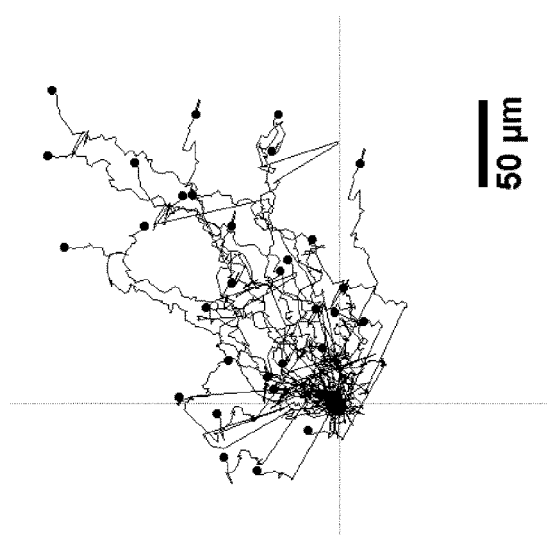
FIG. 6E represents cell tracks from automated cell tracking normalized to a common origin when performing automated cell distribution and tracking analysis of neutrophil chemotaxis.

Although this method did not necessarily reflect chemotaxis strength, it provided a simple way to distinguish random migration and chemotaxis in a relatively noisy system, as shown by the significantly higher Chemotaxis Score in IL-8 gradient compared to medium or uniform IL-8 control (FIG. 5C). These results are consistent with the manual tracking analysis. The automated analysis method can be flexibly modified to suite the need of the experiments. Ultimately, more sophisticated and automated cell motion analysis methods should be developed and incorporated to allow more accurate and quantitative cell migration assessment. Toward this direction, automated single cell tracking analysis was successfully demonstrated in a preliminary experiment (FIG. 6E). However, such highly automated and quantitative analysis has higher requirements for cell migration image sequences and sophisticated tracking algorithms may be developing for further generations of the system.

Discussion

UMCAS is a portable, low-cost and remote controllable microfluidic system for cell migration studies comparing to the traditional systems. The system offers attractable features for the scientists who want to investigate cell migration studies using microfluidic platform. As the technology develops, it is believed that more precision USB microscopes will appear and the image resolution of the system will continue to improve for the next generation of the system. The standalone microfluidic device provides an easy and rapid way to generate chemical gradient. It can maintain a stable gradient for about 45 minutes which is enough for testing fast migrating cells. And the big solution reservoirs could be sealed by PMDS pieces if contamination of the solution is a critical problem. For the cells which need long time to migrate, other designs of microfluidic device are also compatible to UMCAS. The cost and the dimension of UMCAS can be further decreased after more considerate design. The automatic distribution method is a rapid method for the cell chemotaxis analysis. For the cells like neutrophils which show strong directional migration in the chemical gradient, this method is useful as it can give a direct trend of the cell migration during the experiment. For the cells which don't show fast and strong direction migration, as UMCAS can save the time-lapse images in the hard disk, traditional manual tracking could be used to calculate the characteristic parameters such as C.I. and velocity to represent the chemotaxis. Alternatively the software can be further developed to track single cells. Furthermore, more and more studies show the relations between the cell migration and diseases. UMCAS could be further modified as diagnosis tools which can be used in the clinic applications. For example, alteration of neutrophil motility and chemotaxis is associated with patients after burn-injury. On the other hand, increased neturophil chemotaxis and recruitment to specific tissues result in tissue damages and autoimmune problems. Therefore, rapid chemotaxis testing offered by the developed UMCAS system has the potential to be used as disease diagnostic and monitoring markers that will complement the current gold standard methods. The remote monitoring module also meets the demanding for POC testing and can be further developed for long range data transmission.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A microfluidic device for generating a chemical gradient, the device comprising:
a transparent substrate;
a gradient channel formed in the substrate and which is elongate in a longitudinal direction, the gradient channel including a first boundary and a second boundary spanning a length of the gradient channel in the longitudinal direction, the first boundary and the second boundary being spaced apart from one another in a gradient direction so as to define a single chamber that is uniform between the first and second boundaries along a length of the gradient channel in the longitudinal direction;
a first inlet channel which is elongate in the longitudinal direction so as to lie parallel to and spaced outwardly from the first boundary of the gradient channel, the first inlet channel defining a single chamber that is uniform across a width and along a length of the chamber in the longitudinal direction;
a second inlet channel which is elongate in the longitudinal direction so as to lie parallel to and spaced outwardly from the second boundary of the gradient channel, the second inlet channel defining a single chamber that is uniform across a width and along a length of the chamber in the longitudinal direction;
a first inlet well formed in the substrate so as to define a source well in communication with the first inlet channel;
a plurality of first microfluidic channels formed in the substrate in communication between the first inlet channel and the gradient channel at spaced apart positions along the first boundary;

a second inlet well formed in the substrate so as to define a sink well in communication with the second inlet channel;

a plurality of second microfluidic channels formed in the substrate in communication between the second inlet channel and the gradient channel at spaced apart positions along the second boundary; and at least one outlet well formed in the substrate so as to be in fluid communication with gradient channel at an intermediate location between the first and second boundaries;

whereby a chemical gradient is arranged to be generated across the gradient channel by diffusion in the gradient direction between the first and second boundaries of a chemical introduced into the first inlet well.

2. The device according to claim 1 wherein the microfluidic channels are elongate in the gradient direction so as to be oriented transversely to the longitudinal direction of the gradient channel.

3. The system according to claim 1 wherein the microfluidic channels are equidistant in length between the respective inlet channels and the gradient channel.

4. The system according to claim 1 wherein each first microfluidic channel communicates with the gradient channel at a respective location along the first boundary which is offset in the longitudinal direction of the first and second boundaries in relation to locations of corresponding second channels along the second boundary.

5. The system according to claim 1 wherein the first and second inlet wells are symmetrical about a longitudinal direction of the gradient channel in relation to one another.

6. The system according to claim 1 wherein said at least one outlet well comprises two outlet wells in communication with the gradient channel at longitudinally opposed ends of the first and second boundaries.

7. A microfluidic device for generating a chemical gradient, the device consisting of:

a transparent substrate;

a gradient channel formed in the substrate and which is elongate in a longitudinal direction, the gradient channel including a first boundary and a second boundary spanning a length of the gradient channel in the longitudinal direction, the first boundary and the second boundary being spaced apart from one another in a gradient direction so as to define a single chamber that is uniform across a width of the gradient channel between the first and second boundaries along a length of the gradient channel in the longitudinal direction;

a first inlet channel which is elongate in the longitudinal direction so as to lie parallel to and spaced outwardly from the first boundary of the gradient channel, the first inlet channel defining a single chamber that is uniform across a width and along a length of the chamber in the longitudinal direction;

a second inlet channel which is elongate in the longitudinal direction so as to lie parallel to and spaced outwardly from the second boundary of the gradient channel, the second inlet channel defining a single chamber that is uniform across a width and along a length of the chamber in the longitudinal direction;

a first inlet well formed in the substrate so as to define a source well in communication with the first inlet channel;

a plurality of first microfluidic channels formed in the substrate in communication between the first inlet channel and the gradient channel at spaced apart positions along the first boundary;

a second inlet well formed in the substrate so as to define a sink well in communication with the second inlet channel;

a plurality of second microfluidic channels formed in the substrate in communication between the second inlet channel and the gradient channel at spaced apart positions along the second boundary; and two outlet wells formed in the substrate so as to be in fluid communication with gradient channel at longitudinally opposed ends of the first and second boundaries, each outlet well communicating with the gradient channel at an intermediate location across the width between the first and second boundaries;

whereby a chemical gradient is arranged to be generated across the gradient channel by diffusion in the gradient direction between the first and second boundaries of a chemical introduced into the first inlet well.

* * * * *